US011390607B2

United States Patent
Ehlers et al.

(10) Patent No.: US 11,390,607 B2
(45) Date of Patent: Jul. 19, 2022

(54) PROCESS TO PREPARE PROPYLENE AMINES AND PROPYLENE AMINE DERIVATIVES

(71) Applicant: NOURYON CHEMICALS INTERNATIONAL B.V., Arnhem (NL)

(72) Inventors: Ina Ehlers, Stenungsund (SE); Eike Nicolas Kantzer, Uddevalla (SE); Rolf Krister Edvinsson, Partille (SE); Hendrik Van Dam, Ede (NL); Karl Fredrik Lake, Södertälje (SE); Antoon Jacob Berend Ten Kate, Arnhem (NL); Michiel Jozef Thomas Raaijmakers, Deventer (NL); Rens Veneman, Amersfoort (NL); Slavisa Jovic, Utrecht (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,374

(22) PCT Filed: Aug. 7, 2018

(86) PCT No.: PCT/EP2018/071327
§ 371 (c)(1),
(2) Date: Feb. 11, 2020

(87) PCT Pub. No.: WO2019/030197
PCT Pub. Date: Feb. 14, 2019

(65) Prior Publication Data
US 2020/0361910 A1   Nov. 19, 2020

(30) Foreign Application Priority Data

Aug. 11, 2017   (EP) .................................. 17186007

(51) Int. Cl.
*C07D 295/10* (2006.01)
*C07D 403/08* (2006.01)
*C07D 403/06* (2006.01)
*C07D 233/36* (2006.01)
*C07D 239/10* (2006.01)

(52) U.S. Cl.
CPC ......... *C07D 403/06* (2013.01); *C07D 233/36* (2013.01); *C07D 239/10* (2013.01)

(58) Field of Classification Search
CPC ............................ C07D 403/08; C07D 295/10
See application file for complete search history.

(56) References Cited

U.S. PATENT DOCUMENTS 4,503,250 A   3/1985   Herdle
5,491,263 A   2/1996   Rooney et al.

FOREIGN PATENT DOCUMENTS

WO   2013110092 A1   7/2013

OTHER PUBLICATIONS

Bhanage et al. (Green Chemistry, 2003, 5, 340-342).*
Hatchell, D., et al., "Thermal Degradation of Linear Amines for CO2 Capture", Energy Procedia, 2014, pp. 1558-1568, vol. 63.
Wu, C., et al. "Synthesis of urea derivatives from amines and CO2 in the absence of catalyst and solvent", Green Chemistry, 2010, pp. 1811-1816, vol. 12.

* cited by examiner

*Primary Examiner* — Bruck Kifle
(74) *Attorney, Agent, or Firm* — Lorenz & Kopf, LLP

(57) ABSTRACT

A process is provided to prepare propylene amines of the formula $NH_2$—$(A-NH-)_p R$, wherein R is a hydrogen atom or an alkyl group, p is at least 1 when R is an alkyl group, and at least 2 when R is a hydrogen atom, or derivatives or precursors thereof wherein one or more units —NH-A-NH— may be present as a cyclic urea unit

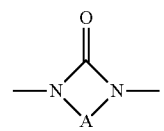

or a cyclic unit

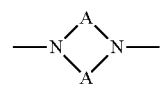

or between two units —NH-A-NH— a carbonyl bond is present, each unit -A- can be independently an alkylene unit and at least one unit -A- is a —$C_3H_6$— unit, wherein each —$C_3H_6$— unit can be linear or branched. The process includes reacting (i) at least one of a hydroxy-functional compound chosen from the alkanolamine-functional compounds, and dihydroxyalkylene compounds, with (ii) an amine-functional compound, in the presence of (iii) a carbon oxide delivering agent, wherein at least one of the alkanolamine-functional compound, the amine-functional compound and/or the carbon oxide delivering agent contains at least one alkylene unit (A) that is a propylene unit.

20 Claims, No Drawings

PROCESS TO PREPARE PROPYLENE AMINES AND PROPYLENE AMINE DERIVATIVES

CROSS-REFERENCE TO RELATED APPLICATION

This application is a U.S. National-Stage entry under 35 U.S.C. § 371 based on International Application No. PCT/EP2018/071327, filed Aug. 7, 2018, which was published under PCT Article 21(2) and which claims priority to European Application No. 17186007.5, filed Aug. 11, 2017, which are all hereby incorporated in their entirety by reference.

TECHNICAL FIELD

The present invention relates to a process for making higher propylene amines (PA), i.e. propylene amines and derivatives (or precursors, which is included by the term derivatives) thereof, like urea derivatives, that contain at least 2 alkylene units of which at least one is a propylene unit, by reacting an hydroxy functional compound with an amine functional compound in the presence of a carbon oxide delivering agent.

BACKGROUND

Propylene amines consist of two or more nitrogen atoms linked by linear or branched propylene units (propylene refers to either —CH$_2$CH$_2$CH$_2$— (P) or —CH(CH$_3$)—CH$_2$— (iP or isopropylene). Propylene amines can be present in the form of linear chains H$_2$N(—C$_3$H$_6$NH)$_p$—H. For p=1, 2, 3, 4, . . . these are denoted PDA, DPTA, L-TPTA, L-TPPA, . . . . For the branched, the isopropylene, these become iPDA, DiPTA, L-TiPTA, L-TiPPA. Compounds with mixed linear and branched C3 units are also possible.

Propylene amines for the sake of this document include alkylene amines in which at least part of the alkylene units are propylene units. Propyleneamines hence also cover amines wherein other alkylene units can be present, like ethylene units. It should also be noted that a propylene unit can be either linear or branched, wherein the branched propylene can also be denoted as methylethylene or isopropylene.

With three or more alkylene units it is possible to create branched propylene amines such as N(C$_3$H$_6$)$_3$, TAPA. Two adjacent nitrogen atoms linked by two ethylene units are called a piperazine ring

which can also be formed for an isopropylene based amine for example

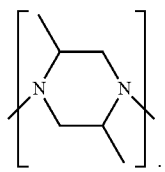

Piperazine rings can be present in longer chains to produce the corresponding cyclic propylene amines. When having linear propylene units, also cyclic structures can be formed like diazocane groups.

Two adjacent nitrogen atoms linked by one propylene unit and one carbonyl moiety form a cyclic urea (U)

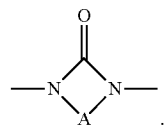

A propylene amine (PA) in which two nitrogen atoms are linked intramolecular by a carbonyl moiety is here referred to as an UPA (urea propylene amine or propylene urea). Replacing the carbonyl moiety with two hydrogen atoms yields the corresponding propylene amine. For example: PU↔PDA, UDPTA↔DPTA, UAPPA↔APPA, UTPTA↔L-TPTA, UTPPA↔L-TPPA. Some higher amines host more than one carbonyl moiety, e.g. DU-TPTA the cyclic diurea of tripropylenetetramine. The carbonyl moiety may link nitrogen atoms on two separate molecules. For example H$_2$NC$_3$H$_6$NH—CO—NHC$_3$H$_6$NH$_2$ and replacing the carbonyl moiety with two hydrogen atoms here yields two PDA.

Each amine function in propylene amines and propylene ureas can be primary, secondary or tertiary. Furthermore, a secondary amine can be linear (linear secondary amines, LSA) or cyclic (cyclic secondary amine, CSA).

In the presence of any Brønsted acid (such as water) propylene amines (PA) can be protonated (PAR$^+$). If not otherwise stated the term amine in this document will include both the protonated and unprotonated form.

Some propylene amines and urea derivatives thereof are shown below as an illustration. This can naturally be extended to include pentamines, hexamines and so on.

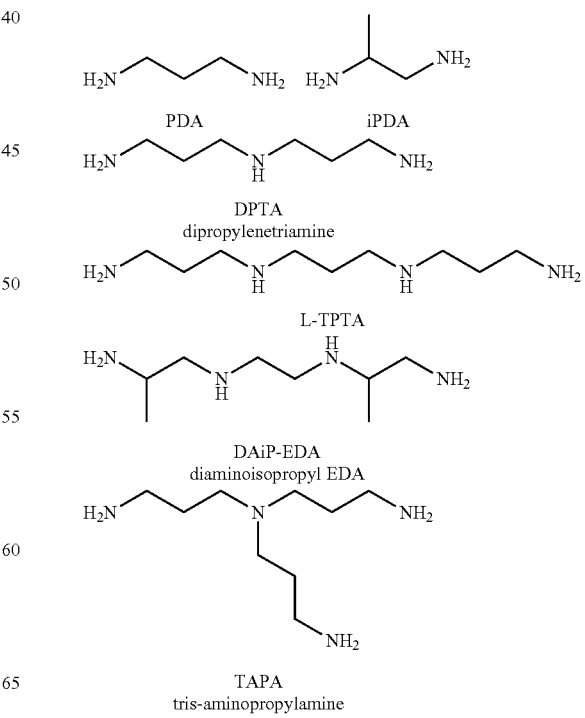

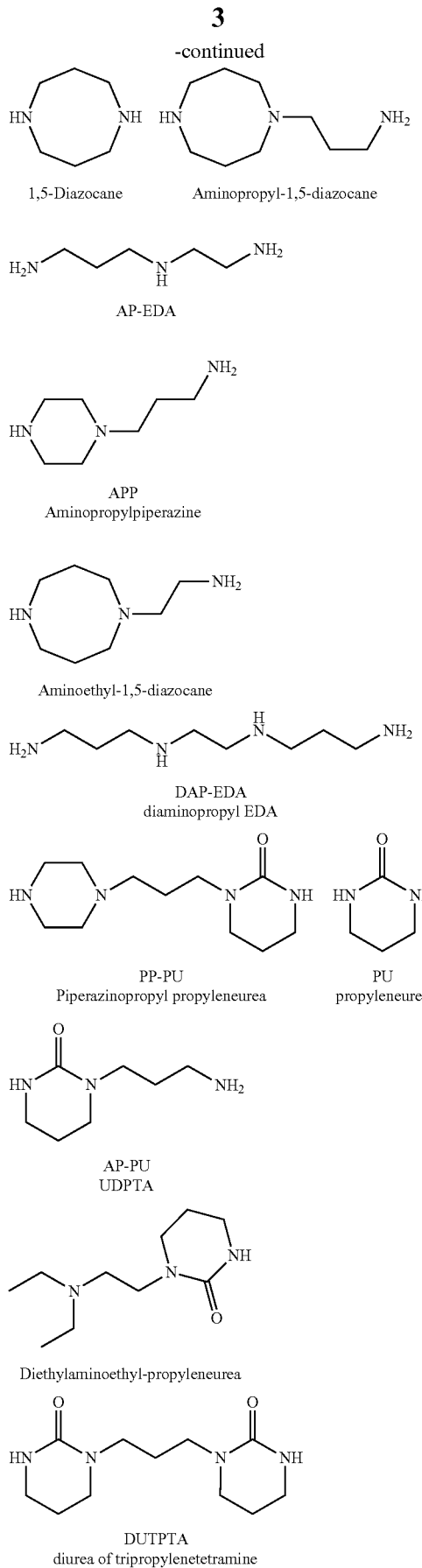

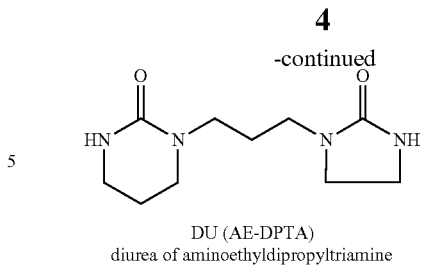

DU (AE-DPTA)
diurea of aminoethyldipropyltriamine

As to naming of the molecules, PDA stands for propylenediamine, and iPDA for isopropylenediamine, DPTA for dipropylenetriamine, L-TPTA for linear tripropylenetetraamine, DAiP-EDA for diamineisopropyl ethylenediamine. TAPA for triaminopropylamine, AP-EDA for aminopropylethylenediamine, APP for aminopropylpiperazine, DAP-EDA for diaminopropylethylenedaimine, PP-PU for piperazinopropyl propyleneurea, PU for propyleneurea, AP-PU for aminopropyl-propyleneurea, DUPTA for the diurea of tripropylenetetramine, DU(AE-DTPA) for the diurea of aminoethyldipropyltriamine When there is a single cyclic urea in the molecule this is indicated by adding a U in front of the name, i.e. UTPTA means the cyclic urea of TPTA, while when there are two cyclic ureas in the molecule this is indicated by DU, i.e. DUTPTA means the internal cyclic diurea of TPTA. If there is a number indicated for the U this refers to the amino group where the U group is located. There is one exception to this naming and that is that instead of UPDA the abbreviation PU is used, which stand for propyleneurea.

The manufacturing of propylene amines is presently disclosed to be done by two routes. These are the reaction of dichloropropanes (1,2- and 1,3-dichloropropane) with NH3 or the reaction of an alkylene amines with acrylonitrile and subsequent hydrogenation.

There are however many limitations in the above state of the art routes, like chloride based processes have severe limitations if only because C1-C3H6-NH2 self-polymerizes very easily, and chloride based processes lead to salt (waste) formation.

The application of acrylonitrile involves a tricky hydrogenation reaction and side product formation from addition reactions with amines (also the intermediate C=N is amine reactive). Again this process suffers from poor control and selectivity.

Furthermore, handling of hazardous acrylonitrile is a risk, because acrylonitrile is a.o. highly flammable and toxic at low doses, can undergo explosive polymerization, is a suspected carcinogenic compound, evaporates quickly at room temperature (20° C.) to easily reach dangerous concentrations.

AlChEAnnual Meeting Conference 2012 'In Situ synthesis of useful amines for CO2 capture from piperazine' discloses the oxazolidinone formation for an ethanolamine and a propanolamine and next shows how an oxazolidinone can react with an amine.

U.S. Pat. No. 4,503,250 discloses the formation of linear polyalkylene amines in good yield by reaction of an alkyleneamine or ammonia with an alcohol or alkanolamine in the presence of derivative of carbonic acid. The alkanolamine covers propanolamines but only ethylene-based explicit examples are mentioned. The alkyleneamine also covers propylene amines, but again only ethylene-based explicit examples are given. None of the Examples mentions the reaction of propylene-based amines or alcohols either.

U.S. Pat. No. 5,491,263 discloses the formation of substituted ethylenediamines such as substituted EDA, DETA, TETA, TEPA, PEHA, E-100 and piperazine by reacting oxazolidinones with alkanolamines or secondary amines. The document also suggests isopropylene amine preparations, but such reactions are not explicitly disclosed and hence not enabled, the document seems to more focus on reacting oxazolidinones having a substituent on the nitrogen atom to create branched amines (called dimers and trimers).

Though all the above documents make a suggestion that the reactions disclosed in them could be performed to prepare propyleneamines, none of them actually demonstrates such reactions or gives the conditions needed for them to be carried out It should be noted that WO2013/110092 discloses in Example 7 the oxazolidinone structures of monoisopropanol amine or monopropanol amine and their reaction product with piperazine, i.e. an amine-functional compound with a terminal cyclic urea unit, under non-aqueous conditions.

There is a demand for propylene amines and hence there is a need for a process for selectively making such propylene amines with an improved yield. Especially there is a need for a process to prepare specific higher linear propylene amines with good yield and selectivity. Furthermore there is a need for such a process for making higher propylene amines that does not co-generate large amounts of waste salt.

BRIEF SUMMARY

A process is provided to prepare propylene amines of the formula $NH_2-(A-NH-)_pR$, wherein R is a hydrogen atom or an alkyl group, p is at least 1 when R is an alkyl group, and at least 2 when R is a hydrogen atom, or derivatives or precursors thereof wherein one or more units —NH-A-NH— may be present as a cyclic urea unit

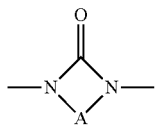

or a cyclic unit

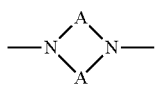

or between two units —NH-A-NH— a carbonyl bond is present, each unit -A- can be independently an alkylene unit and at least one unit -A- is a —$C_3H_6$— unit, wherein each —$C_3H_6$— unit can be linear or branched. The process includes reacting (i) at least one of a hydroxy-functional compound chosen from the alkanolamine-functional compounds, and dihydroxyalkylene compounds, with (ii) an amine-functional compound, in the presence of (iii) a carbon oxide delivering agent, wherein at least one of the alkanolamine-functional compound, the amine-functional compound and/or the carbon oxide delivering agent contains at least one alkylene unit (A) that is a propylene unit.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The present invention now provides a process to prepare propylene amines of the formula $NH2-(A-NH-)pR$, wherein R is a hydrogen atom or an alkyl group, p is at least 1 when R is an alkyl group, and at least 2 when R is a hydrogen atom, or derivatives or precursors thereof wherein one or more units —NH-A-NH— may be present as a cyclic urea unit

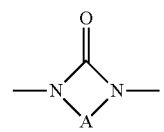

or a cyclic unit

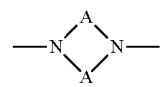

or between two units —NH-A-NH— a carbonyl bond is present, each unit -A- can be independently an alkylene unit and at least one unit -A- is a —$C_3H_6$— unit, wherein each —$C_3H_6$— unit can be linear or branched, by reacting (i) at least one of a hydroxy-functional compound chosen from the alkanolamine-functional compounds, and dihydroxyalkylene compounds, with (ii) an amine-functional compound in the presence of (iii) a carbon oxide delivering agent, wherein at least one of the alkanolamine-functional compound, the amine compound and/or the carbon oxide delivering agent contains at least one alkylene unit (A) that is a propylene unit.

The process of the invention solves all the above indicated problems and leads to the production of propylene amines in good yield and selectivity. The process is moreover based on chemical compounds that have a better HSE (health safety and environment) profile (ethanol- and propanolamines e.g. have a very low mutagenic potential) than the mentioned state of the art processes. Besides, the present process provides for increased flexibility in producing different types of higher amines, like, combining different alkylene units, like ethylene and propylene and cyclic units in a very controlled manner under relatively mild reaction conditions.

The product of the process of the invention is in this document sometimes referred to as polypropylene amine as well as as propylene amine. Still these terms refer to the same group of compounds. Furthermore as should also be clear from the embodiments, a product propyleneamine or polypropylene amine may contain hydroxyl groups, and may contain a terminal alkyl group.

Selecting the right molar ratios between the carbon oxide delivering agent, amine-functional compound and hydroxy-functional compound, was found to have an effect on conversion, selectivity and yield in the process of the invention.

The molar amount of either one of these carbon oxide delivering agent, amine-functional compound and hydroxy-functional compound is determined by the reactants in the process, independent of the dosing regime used for the reactants.

In a preferred embodiment the molar ratio of carbon oxide delivering agent to amine-functional compound is at least 0.6 to 1. In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

It was found that when adding at least 0.6 molar equivalents of carbon oxide delivering agent on amine-functional compound, the yield of propylene amines increases considerably and also the amount of side products decreases, i.e. the selectivity of the reaction towards specific propylene amines increases.

In this embodiment it is more preferred that the molar amount of carbon oxide delivering agents on amine-functional compounds is between 0.7 and 20 molar equivalents of carbon oxide delivering agent on moles of amine functional compound, and yet more preferably it is between 0.7 and 6:1, most preferably between 0.8:1 and 3:1.

In another preferred embodiment the molar ratio of hydroxy-functional compound to amine-functional compound is at least 0.7:1 and the molar ratio of carbon oxide delivering agent to amine-functional compound is at least 0.05:1. In such embodiments the yield of propylene amines is also high.

In this embodiment, more preferably the molar ratio of hydroxy-functional compound to amine-functional compound is between 0.8 and 5:1 and the molar ratio of carbon oxide delivering agent to amine functional compound is between 0.2:1 and 20:1.

Yet even more preferably the molar ratio of hydroxy-functional compound to amine-functional compound is between 1:1 and 2:1 and the molar ratio of carbon oxide delivering agent to amine-functional compound is between 0.7:1 and 3:1

To achieve a high selectivity of propylene amine product on starting materials, especially on hydroxy-functional compound, in another preferred embodiment the molar ratio of hydroxy-functional compound to amine-functional compound is between 0.05:1 and 0.7:1 and the molar ratio of carbon oxide delivering agent to amine-functional compound is higher than the molar ratio of hydroxy-functional compound to amine-functional compound.

In this embodiment, more preferably the molar ratio of carbon oxide delivering agent to amine-functional compound is at least 10% higher, even more preferably at least 50%, than the molar ratio of hydroxy-functional compound to amine-functional compound. In yet another more preferred embodiment the molar ratio of hydroxy-functional compound to amine-functional compound is between 0.1 and 0.5.

It should be noted that compounds exist that contain more than one carbonyl group that can be released from the molecule for transfer to the hydroxy-functional compound, such as for example DU-TPTA. When determining the molar ratio for such compounds there should be an adjustment for the molar amount of carbon oxide they can release for transfer to the hydroxy-functional compound. Accordingly, 1 mole of DU-TPTA should be considered 2 moles of carbon oxide delivering agent.

The reaction mixture characterized by containing as reactants hydroxy-functional compound, amine-functional compound and carbon oxide delivering agent can be roughly represented by below (non-limiting) schemes.

Schemes 1A and 1B: Amine functional compound is a primary ethyleneamine, respectively propyleneamine

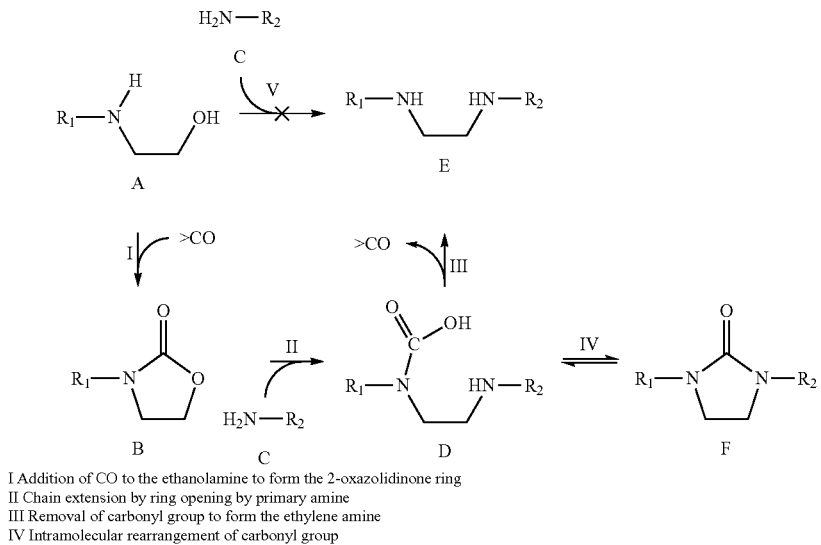

I Addition of CO to the ethanolamine to form the 2-oxazolidinone ring
II Chain extension by ring opening by primary amine
III Removal of carbonyl group to form the ethylene amine
IV Intramolecular rearrangement of carbonyl group
V Hypothetical direct uncatalyzed amination

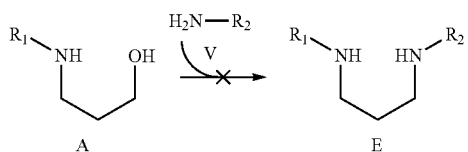

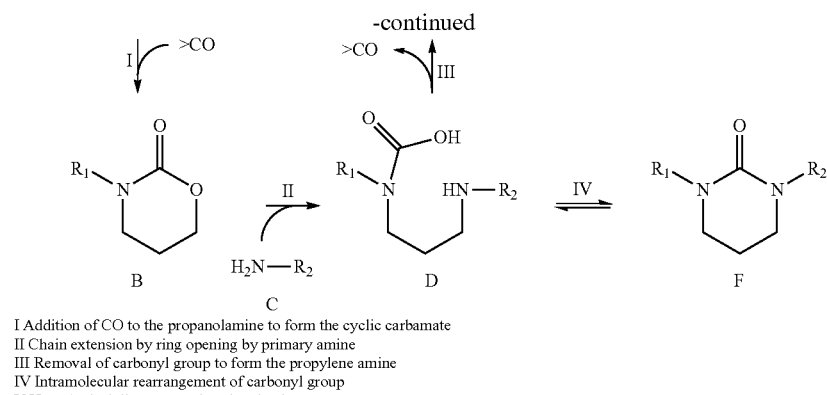

B     C     D     F

I Addition of CO to the propanolamine to form the cyclic carbamate
II Chain extension by ring opening by primary amine
III Removal of carbonyl group to form the propylene amine
IV Intramolecular rearrangement of carbonyl group
V Hypothetical direct uncatalyzed amination Schemes 2A and 2B: Amine functional compound is a Cyclic Secondary Amine

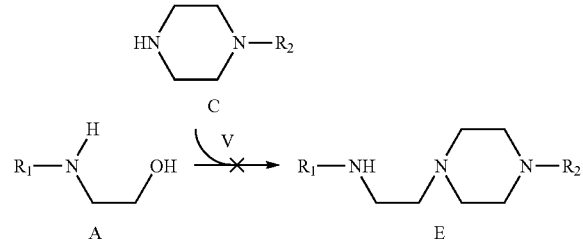

A     E

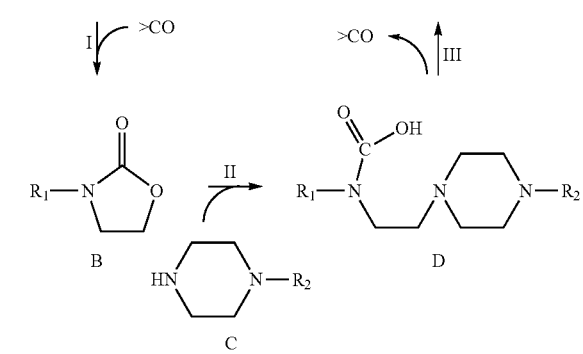

B     C     D

I Addition of CO to the ethanolamine to form the 2-oxazolidinone ring
II Chain extension by ring opening by cyclic secondary amine
III Removal of carbonyl group to form the ethylene amine
V Hypothetical direct uncatalyzed amination

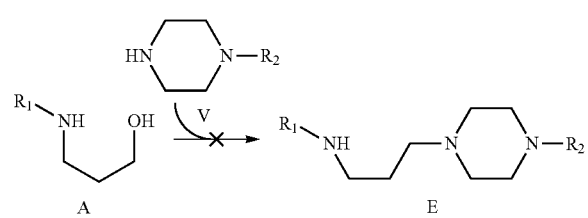

A     E

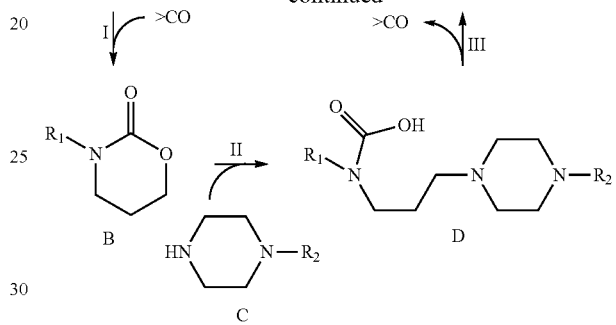

B     C     D

I Addition of CO to the propanolamine to form the cyclic carbamate
II Chain extension by ring opening by cyclic secondary amine
III Removal of carbonyl group to form the propylene amine
V Hypothetical direct uncatalyzed amination A number of reactions take place in parallel when heating a mixture of a carbonyl source, a hydroxy-functional compound and an amine-functional compound.

Without being bound to theory this can be summarized in two main reaction steps each composed of multiple sub steps: 1) the activation of the alcohol function (A) by the carbonyl group, the carbamate compound (B) is assumed to be an intermediate, 2) the activated alcohol function is replaced by an amine (C) to give a chain extended primary addition product (D). In the presence of ammonia a conversion of the alcohol function to an amine function without giving a chain extension can take place as well. The product (D) may undergo further reaction leading to secondary CO containing products as illustrated by reaction IV and product (F). Such products include but are not limited to cyclic propylene urea derivatives but include all kinds of CO containing amines as for example illustrated in below examples of CO delivering agents. Optionally the CO groups can be removed leading to the formation of a propylene amine (E).

The dihydroxyalkylene compound in preferred embodiments is selected from the group of dihydroxyethane, 1,2-dihydroxypropane and 1,3-dihydroxypropane.

The alkanolamine-functional compound is a compound containing a hydroxyl group linked via an alkylene to an amine group that optionally may be present as its carbamate equivalent. Generally the alkanolamine-functional compound is of the following formula OH—(A-NH—)qR Where R in embodiments is a substituted or unsubstituted alkyl group which also can contain unsaturated moieties and heteroatoms such as oxygen and nitrogen or a hydrogen atom, q is at least 1, and A is an alkylene unit, and at least one A is propylene. In one embodiment R is a proton or hydroxyalkyl group.

Examples of alkanolamine functional compounds include

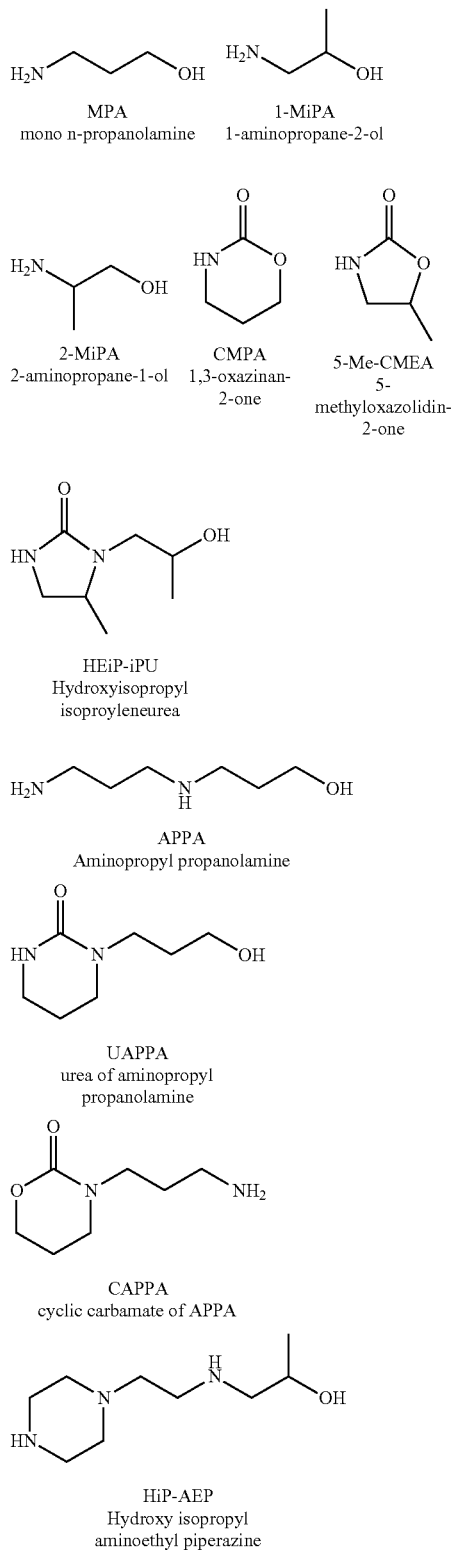

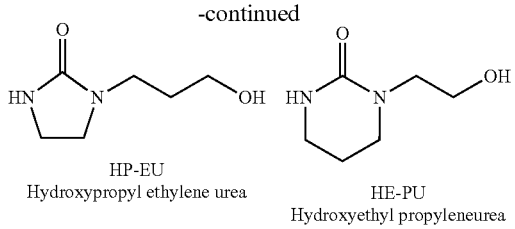

As to naming convention, MPA stands for monopropanolamine, 1-MiPA stands for 1-aminopropan-2-ol, 2-MiPA stands for 2-aminopropan-1-ol, CMPA stands for 1,3-oxazinan-2-one, 5-Me-CMEA stands for 5-methyloxazolidin-2-one, HEiP-iPU stands for hydroxyisopropylisopropyleneurea, APPA stands for aminopropylpropanolamine (also referred to as hydroxypropylpropyleneamine), HiP-AEP stands for hydroxyl isopropyl aminoethylpiperazine, HP-EA stands for hydroxypropyl ethyleneurea and HE-PU stands for hydroxyethyl propyleneurea. By using the letter C it is indicated that a cyclic carbamate ring is present in the molecule. By using the letter U it is indicated that a cyclic urea ring is present in the molecule.

The carbon oxide delivering agent is a compound containing a carbonyl moiety that can be transferred to an alkanolamine functional compound leading to the formation of a cyclic carbamate, such as CMPA or that can be transferred to an amine leading to the formation of the corresponding cyclic urea. Next to cyclic compounds linear carbamates and ureas may form as well.

Carbon oxide delivering agents within the scope of the present invention include organic compounds in which a carbonyl moiety is available for being transferred as described above. Organic compounds in which a carbonyl moiety is available for being transferred include carbon dioxide, and urea and derivatives thereof linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is $CO_2$, a cyclic alkylene urea or cyclic alkylene carbamate, optionally wherein part of the alkylene is propylene, or urea or propylene carbonate, more preferably the carbon oxide delivering agent is at least partly added as carbon dioxide or urea. The carbon oxide delivering agent can be present in the process in the same molecule as the amine functional or the alkanolamine functional compound by using the aforementioned urea or carbamate compounds.

Examples of carbon oxide delivering agents include

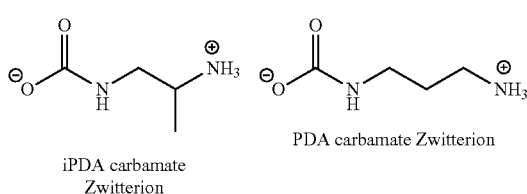

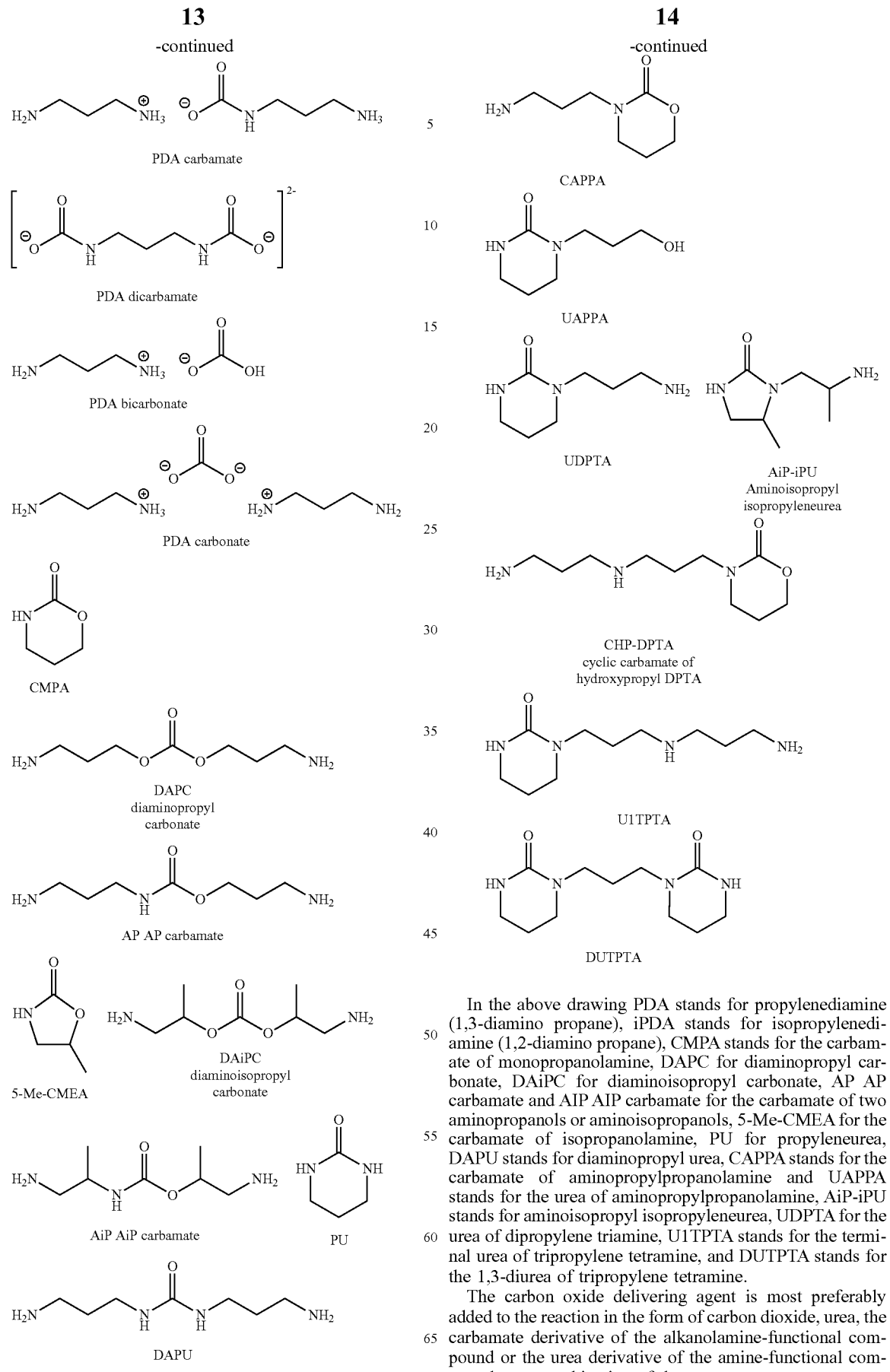

In the above drawing PDA stands for propylenediamine (1,3-diamino propane), iPDA stands for isopropylenediamine (1,2-diamino propane), CMPA stands for the carbamate of monopropanolamine, DAPC for diaminopropyl carbonate, DAiPC for diaminoisopropyl carbonate, AP AP carbamate and AIP AIP carbamate for the carbamate of two aminopropanols or aminoisopropanols, 5-Me-CMEA for the carbamate of isopropanolamine, PU for propyleneurea, DAPU stands for diaminopropyl urea, CAPPA stands for the carbamate of aminopropylpropanolamine and UAPPA stands for the urea of aminopropylpropanolamine, AiP-iPU stands for aminoisopropyl isopropyleneurea, UDPTA for the urea of dipropylene triamine, U1TPTA stands for the terminal urea of tripropylene tetramine, and DUTPTA stands for the 1,3-diurea of tripropylene tetramine.

The carbon oxide delivering agent is most preferably added to the reaction in the form of carbon dioxide, urea, the carbamate derivative of the alkanolamine-functional compound or the urea derivative of the amine-functional compound, or a combination of these.

Heating a suitable mixture of an alkanolamine-functional compound, an amine that is not tertiary and a carbon oxide delivering agent to a relatively high temperature provides a way to produce a higher amine and CO containing derivative thereof that can serve as a carbon oxide delivering agent.

The amine-functional compound is a compound containing one or more amine groups, preferably at least two amine groups, and no alcohol groups.

In many embodiments the amine-functional compound is a compound of the formula RRN—(A-NR-)rR wherein r is at least 1, each R is independently as defined above for the alkanolamine compound provided that it does not contain any hydroxyl groups, i.e. R in embodiments is a substituted or unsubstituted alkyl group which also can contain unsaturated moieties and heteroatoms such as oxygen and nitrogen or a hydrogen atom, and preferably all R groups are hydrogen or one terminal R is an alkyl group while the other R groups are a hydrogen atom, and A is as defined above for the alkanolamine compound. Many compounds illustrated above as propylene amine compounds are amine-functional compounds as well.

In a preferred embodiment the amine-functional compound is a compound containing at least two amine groups. Even more preferred the amine-functional compound contains at least two amine groups that are independently a primary amine group or cyclic secondary amine group, and optionally more amine groups that may be primary, secondary and/or tertiary amines wherein the amine groups within the compound are linked to one another via alkylene groups, and optionally some by a carbonyl moiety, and/or an additional alkylene group (to give a methylsubstituted or unsubstituted piperazine unit, a diazocane unit, or urea unit in the amine functional compound).

In another preferred embodiment the amine-functional compound is a compound of the formula R—NH2, wherein R is a substituted or unsubstituted, linear or branched alkyl group which also can contain unsaturated moieties and heteroatoms such as oxygen and nitrogen but does not contain a hydroxyl group. Yet even more preferred R is an alkyl group, that may be branched or linear, and that in embodiments contains 6 to 22 carbon atoms.

In a further preferred embodiment in the process the alkanolamine-functional compound is of the formula OH—(A-NH-)qH wherein q is at least 1 and the amine-functional compound is of the formula NH2-(A-NH-)rH wherein r is at least 1, wherein the sum of q+r is at least 2, more preferably q+r is at least 3, each A unit is independently a —C2H4- unit or —C3H6- unit and at least one A unit is a —C3H6- unit, and each C3H6 unit can be linear or branched, and wherein optionally one or more q or r units may be present as a cyclic propylene urea, cyclic propylene carbamate, methylsubstituted piperazine unit, diazocane unit, or unsubstituted piperazine unit.

In another preferred embodiment the alkanolamine-functional compound and the carbon oxide delivering agent are at least partly added as one compound by using a carbamate adduct and/or the amine-functional compound and the carbon oxide delivering agent are at least partly added as one compound by using an urea adduct.

In embodiments wherein the amine-functional compound is a compound containing a terminal cyclic unit

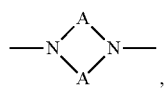

i.e. a compound containing the above cyclic unit wherein at least one nitrogen is bound to a hydrogen atom, the process of the present invention is preferably performed in a liquid that contains water, even more preferably at least 75 wt % of water on total liquid weight. In yet another preferred embodiment wherein the amine-functional compound is a compound containing a terminal cyclic unit

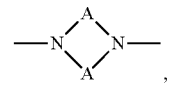

the molar ratio of water to the amine-functional compound containing the terminal cyclic unit is greater than 0.2:1, preferably greater than 0.5:1 and most preferably greater than 1:1.

In embodiments wherein in the reactants (and consequently products) of the process of the invention one or more units —NH—C2H4-NH— are present as a cyclic unit

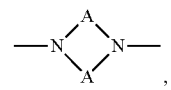

such as in embodiments a unsubstituted or methylsubstituted piperazine unit the reaction is preferably performed in a liquid that comprises water.

Examples of embodiments wherein one or more of the units —NH-A-NH— are present as a piperazine unit is when the amine-functional compound is piperazine (PIP), aminoethylpiperazine (AEP), or diaminoethylpiperazine (DAEP), piperazinoethyl ethylenediamine (PEEDA), or a linear urea derivative thereof or 2-methylpiperazine, 2,5-dimethylpiperazine, 2-(3-methylpiperazin-1-yl)ethan-1-amine, 2-(2,5-dimethylpiperazin-1-yl)ethan-1-amine, 2,2'-(2-methylpiperazine-1,4-diyl)bis(ethan-1-amine), 2,2'-(2,5-dimethylpiperazine-1,4-diyl)bis(ethan-1-amine), N1-(2-(3-methylpiperazin-1-yl)ethyl)ethane-1,2-diamine, N1-(2-(2,5-dimethylpiperazin-1-yl)ethyl)ethane-1,2-diamine or a linear urea derivative thereof or when the alkanolamine-functional compound is an isopropanolamine, 2-amino-1-propanol or 1-amino-2-propanol or diisopropanolamine.

Even more preferably when cyclic/piperazine units are present in the reactants or products of the process of the invention the liquid comprises at least 75 wt-% of water on total liquid weight. In yet another even more preferred embodiment the molar ratio of water to the amine-functional compound is greater than 0.2:1, preferably greater than 0.5:1 and most preferably greater than 1:1.

When preparing propyleneamines that do not contain piperazine units and/or other cyclic units

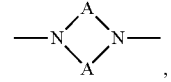

i.e when using reactants that are free from cyclic and/or piperazine units, the process in other preferred embodiments is carried out in water, with a molar ratio of water:carbon oxide delivering agent of from 0.01:1 to 2:1, more preferably a molar ratio of water:carbon oxide delivering agent is between 0.05:1 and 1:1.

It is yet even more preferred that water is added or removed during the process intermittently, semi-continuously or continuously to maintain the amount of water such that the molar ratio of water:carbon oxide delivering agent remains in the desired range such as for non-cyclic propylene amines preparations of from 0.01:1 to 2:1.

When preparing propylene amine compounds having at least 3 alkylene units and using carbon dioxide as the carbon oxide delivering agent, it is a beneficial embodiment of the process to during the reaction wherein the amine-functional compound reacts with CO2 add an auxiliary compound selected from ethylenediamine (EDA), propylenediamine (PDA), monoethanolamine (MEA), monopropanolamine (MPA) and mixtures thereof, the molar ratio of auxiliary compound to amine-functional compound being at least 0.02:1.

In this embodiment, more preferably the molar ratio of auxiliary compound to amine-functional compound is at least 0.05:1, in particular at least 0.1:1, and/or at most 10:1. Yet even more preferred the molar ratio between CO2 and —NH-A-NH— moieties in the amine-functional compound is at least 0.5:1 and/or at most 500:1.

More specifically the above relates to a process to prepare propylene amines or cyclic urea adducts thereof, which process comprises the steps of
a) manufacturing a cyclic urea adduct of an alkylene amine compound and/or alkanolamine compound comprising at least one —NH-A-NH— moiety and at least two A moieties wherein at least one alkylene (A) unit in the product is a propylene unit, wherein the alkylene amine compound is reacted with CO$_2$ in the presence of an auxiliary compound selected from ethylene diamine (EDA), propylenediamine (PDA or iPDA) monoethanolamine (MEA), monopropanolamine (MPA or MiPA) and mixtures thereof, the molar ratio of auxiliary compound to amine-functional compound being at least 0.02:1, and
b1) where the cyclic urea adduct of an alkylene amine compound is a cyclic urea adduct of alkylene amine, reacting the cyclic urea adduct of alkylene amine with an alkanolamine-functional compound, or a urea- or carbamate additive thereof, or
b2) where the cyclic urea adduct of an alkylene amine compound is a cyclic urea adduct of an alkanolamine, reacting the cyclic urea adduct of an alkanolamine with a alkylene amine compound, or a urea- or carbamate additive thereof.

Using the process of the invention it is well possible to prepare tailored mixtures of straight chain and non-straight chain propylene amines wherein the non-straight chain propylene amines can be branched or cyclic propylene amines by a smart selection of the starting material amine-functional compound, alkanolamine-functional compound and carbon oxide delivering agent. This because substantially any branched and cyclic raw materials find their way into the product without losing their branching or cyclic structure and also no substantial new levels of branching and cyclization occur during the process of the invention Accordingly, the present invention also provides a process of preparing a mixture of straight-chain propyleneamines and non-straight-chain propyleneamines selected from branched propyleneamines and cyclic propyleneamines, or the urea derivatives thereof, comprising the step of reacting amine-functional compound with alkanolamine-functional compound in the presence of a carbon oxide delivering agent, wherein a) amine-functional compound comprising a combination of straight-chain amine-functional compound and non-straight-chain amine-functional compound is reacted with straight-chain alkanolamine-functional compound, or
b) straight-chain amine-functional compound is reacted with alkanolamine-functional compound comprising a combination of straight-chain alkanolamine-functional compound and non-straight-chain alkanolamine-functional compound, or
c) amine-functional compound comprising a combination of straight-chain amine-functional compound and non-straight-chain amine-functional compound is reacted with alkanolamine-functional compound comprising a combination of straight-chain alkanolamine-functional compound and non-straight-chain alkanolamine-functional compound In a more preferred embodiment for making tailored mixtures, the amine-functional starting material comprises non-straight-chain amine-functional compound comprising a cyclic amine-functional compound selected from the group of piperazine or methyl substituted piperazine or an alkyleneamine derivative of either of those such as aminoethylpiperazine, diaminoethylpiperazine, piperazinoethylpiperazine, piperazino-ethylethylenediamine, and mixtures thereof, in particular piperazine aminopropylpiperazine and/or aminoethylpiperazine.

The amine-functional starting material comprises non-straight-chain amine-functional compound comprising a branched amino-functional compound comprising at least one tertiary nitrogen atom, e.g., a compound of the formula

wherein each n independently is 0 or an integer, in particular 1, 2, 3, or 4.

The straight-chain amine-functional compound may comprises one or more compounds of the formula HN-(A-NH)$_r$-H, wherein r is at least 1, in particular in the range of 1 to 10, more in particular 1 to 5.

The non-straight-chain ethanolamine-functional compound may comprise a cyclic alkanolamine-functional compound, e.g., a compound selected from the group of hydroxyalkyl derivatives of aminoethylpiperazine (AEP), e.g., piperazinoethylmonoethanolamine (PE-MEA).

The non-straight-chain alkanolamine-functional compound may furthermore comprise a branched alkanolamine-functional compound comprising at least one tertiary nitrogen atom, for example a compound of the formula

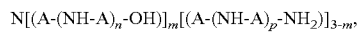

wherein m is 1, or 2, or 3, each n independently is an integer, in particular 1, 2, 3, or 4, and each r independently is 0 or an integer, in particular 1, 2, 3, or 4, in particular a compound m is 1, n is 1, and p is 0.

The straight-chain ethanolamine-functional compound may comprises compounds of the formula HO-(A-NH)q-H wherein q is at least 1, in particular in the range of 1 to 10, more in particular 1 to 5.

In a preferred embodiment for making tailored mixtures the ratio of the total amount of piperazine moieties and methylated piperazine moieties in the starting materials to the total amount of such moieties in the product from the reaction is in the range of 0.7:1 to 1.3:1, in particular in the range of 0.8:1 to 1.2:1, more in particular in the range of 0.9:1 to 1.1:1.

In another preferred embodiment for making tailored mixtures the ratio of the total amount of tertiary amine moieties of the formula N(A-)3 in the starting material to the total amount of tertiary amine moieties of the formula N(A-)3 in the product from the reaction generally is in the range of 0.7:1 to 1.3:1, in particular in the range of 0.8:1 to 1.2:1, more in particular in the range of 0.9:1 to 1.1:1.

In the process of the invention a step may be present in which a cyclic urea adduct of an alkyleneamine compound is first made, the alkyleneamine compound having at least one linear —NH-A-NH— group, and at least one alkylene unit (A) is a propylene unit, and the process comprises the steps of
- in an absorption step contacting a liquid medium comprising an alkyleneamine compound having a linear —NH-A-NH— group with a $CO_2$-containing gas stream at a pressure of 1-20 bar, resulting in the formation of a liquid medium into which $CO_2$ has been absorbed,
- bringing the liquid medium to cyclic urea formation conditions, and in an urea formation step forming cyclic urea adduct of the alkyleneamine compound, urea formation conditions including a temperature of at least 120° C., wherein the total pressure at the end of the urea formation step is at most 20 bar, wherein the temperature in the absorption step is lower than the temperature in the urea formation step.

Contrary to what was expected it was found very well possible to get a good cyclic urea formation under the above mild conditions and under these conditions a suitable carbon oxide delivering agent can be made for use in the further process of the present invention.

Preferably the CO2-containing gas stream comprises at least 95 vol. % of CO2.

The step of contacting the liquid medium with the CO2-containing gas steam in the absorption step is carried out preferably at a temperature between 0° C. and 200° C., in particular at a temperature of at most 190° C., more in particular at most 150° C., or at most 130° C., more in particular at most 110° C. and preferably at a value of at least at least 20° C., in particular at least 40° C.

The maximum total pressure in the absorption step is preferably between 1 and 15 bara, more in particular between 1 and 10 bara, even more in particular between 1 and 3 bara.

The temperature in the urea formation step is suitably at least 140° C., in particular at least 150° C., more in particular at least 170° C. and preferably at most 400° C., in particular at most 300° C., more in particular at most 250° C., or even at most 220° C. and the urea formation step is preferably carried out in a closed vessel or a vessel wherein the volume of the liquid medium in the vessel makes up at least 50% of the total volume of the vessel (including head space), in particular at least 70%, more in particular at least 85%.

Preferably the pressure at the end of the cyclic urea formation step is below 15 bar, in particular below 10 bar, in some embodiments below 5 bar, or even below 3 bar.

In another preferred embodiment urea is used as the carbon oxide delivering agent. The urea is dissolved or dispersed as solid in a vessel together with the liquid comprising alkanol and/or alkylene amine. The temperature in the urea formation step is suitably at least 140° C., in particular at least 150° C., more in particular at least 170° C. and preferably at most 400° C., in particular at most 300° C., more in particular at most 250° C., or even at most 220° C.

The maximum total pressure in the urea reaction step is preferably between 1 and 100 bara, more in particular between 1 and 50 bara, even more in particular between 1 and 10 bara.

The reaction time is preferably between 1 minute and 10 hours, more preferably between 30 minutes and 5 hours.

The cyclic urea or cyclic carbamate formation can be carried out in a closed vessel in which the released ammonia causes a pressure to build up. At the end of the reaction ammonia has to be released and the resulting gas stream is suitably treated to remove or recover the ammonia for further use. More preferably it is carried out in a vessel in equipped in which ammonia is continuously, semi-continuously or on one or several occasions removed from the system and suitably treated or recovered.

The process of the present invention in embodiments may in embodiments be performed as an integrated process for manufacturing polypropylene amine compounds selected from the group of propyleneamines and hydroxyl-functional propyleneamines comprising the steps of
- an adduction step providing a $CO_2$ adduct of a starting compound comprising a —NH-A-NH— moiety or a —NH-A-OH moiety, or HO-A-OH,
- in a reaction step reacting a hydroxy-functional compound selected from the group of alkanolamines, dihydroxyethane, 1,2-dihydroxypropane and 1,3-dihydroxypropane with an amine-functional compound, wherein at least part of the total of hydroxy-functional compounds and amine-functional compounds is provided in the form of a $CO_2$ adduct, to form $CO_2$ adduct of a polypropylene amine compound,
- in an elimination step converting $CO_2$ adduct of polypropylene amine compound to the corresponding polypropylene amine compound,
- wherein a fraction comprising a recycle compound comprising a —NH-A-NH— moiety or a —NH-A-OH moiety, or HO-A-OH, or $CO_2$ adducts thereof, is provided from the end of the reaction step or the elimination step to the adduction step or to the reaction step, the recycle compound having per molecule on average fewer of the total of —NH-A-NH— moieties and —NH-A-OH moieties than the polypropylene amine compound.

In the above integrated process, the adduction step may comprise an absorption step wherein gaseous $CO_2$ is reacted with a starting compound comprising a —NH-A-NH— moiety or a —NH-A-OH moiety, or HO-A-OH, to form a $CO_2$ adduct thereof.

In the above integrated process, the adduction step may comprise the step of reacting starting compound comprising —NH-A-NH— moiety or a —NH-A-OH moiety, or HO-A-OH with a carbon oxide delivering agent which can transfer a carbonyl group to the starting compounds, resulting in the formation of CO2 adducts thereof.

The elimination step in the integrated process may comprise a desorption step in which the CO2 adduct of polypropylene amine compound is reacted with water to form CO2 and the corresponding propylene amine compound.

In another embodiment the elimination step may comprise a caustic treatment step in which CO2 adduct of polypropylene amine compound is reacted with an inorganic base, resulting in the formation of a polypropylene amine compound and a carbonate salt.

In yet another embodiment the elimination step may comprise a CO2 transfer step, wherein the carbonyl group from the CO2 adduct of the polypropylene amine compound is transferred to a compound having a —NH-A-NH— moiety or a NH-A-OH moiety, or HO-A-OH.

In the integrated process the adduction step may comprise an absorption step and the elimination step may comprise a desorption step, wherein CO2 formed in the desorption step is provided at least in part to the absorption step.

In another embodiment the adduction step comprises an absorption step and the elimination step comprises a desorption step, and wherein stripping gas withdrawn from the desorption step is subjected to a CO2 removal step and recycled at least in part to the desorption step.

Preferably, the stripping gas containing CO2 is removed from the desorption step and provided to absorption step, where CO2 is absorbed from the CO2-containing stripping gas, and stripping gas from which CO2 has been removed is withdrawn from the absorption step and provided to the desorption step.

In an embodiment of the integrated process a separation step is provided after the elimination step, the separation step yielding a fraction comprising a recycle compound comprising a —NH-A-NH— moiety or a —NH-A-OH moiety, or HO-A-OH, or CO2 adducts thereof, which fraction is provided in its entirety or in part to the adduction step or to the reaction step, the recycle compound having per molecule on average fewer of the total of —NH-A-NH— moieties and —NH-A-OH moieties than the polypropylene amine compound, the recycle compound comprising starting compounds and optionally intermediate compounds, the separation step further yielding a product fraction of polypropylene amine compounds.

Preferably, a separation step is provided after the reaction step and before the elimination step, the separation step yielding a fraction comprising a recycle compound comprising a —NH-A-NH— moiety or a —NH-A-OH moiety, or HO-A-OH, or $CO_2$ adducts thereof, which fraction is provided in its entirety or in part to the adduction step or to the reaction step, the separation step further yielding a fraction comprising $CO_2$ adduct of polypropylene amine compounds, which fraction is provided to the elimination step.

In another preferred embodiment of the integrated process the elimination step comprises a first elimination step and one or more further elimination steps, wherein the elimination steps are independently selected from the group of
  a desorption step in which the $CO_2$ adduct of polypropylene amine compound is reacted with water to form $CO_2$ and the corresponding ethylene amine compound,
  a caustic treatment step in which $CO_2$ adduct of polypropylene amine compound is reacted with an inorganic base, resulting in the formation of a polypropylene amine compound and a carbonate salt, and
  a $CO_2$ transfer step, wherein the carbonyl group from the $CO_2$ adduct of the polypropylene amine compound is transferred to a compound having a —NH-A-NH— moiety or a NH-A-OH moiety, or HO-A-OH,
  wherein the first elimination step converts part of the $CO_2$ adducts of polypropylene amines present in the feed thereto into the polypropylene amine compounds, while part of the $CO_2$ adducts of polypropylene amines present in the feed to the first elimination step is not converted in the first elimination step, and is provided to a further elimination step.

Even more preferred, the first elimination step is a desorption step or a $CO_2$ transfer step and the further elimination step is a desorption step or a caustic treatment step, wherein the steps are not the same.

In a further preferred embodiment the elimination step yields a product comprising polypropylene amine compounds and $CO_2$ adducts of polypropylene amine compounds, and this product is provided to a separation step where a fraction comprising $CO_2$ adducts of polypropylene amine compounds is separated from the polypropylene amine compounds, and processed in one or more of the following manners:
  it is subjected at least in part to purification and further separation steps,
  it is recycled at least in part to the elimination step,
  it is provided at least in part to a further elimination step which is carried out under more stringent conditions than the first elimination step, and comprises, e.g., a treatment with a strong inorganic base,
  it is provided at least in part to the reaction step.

In an embodiment the starting materials are provided to the reaction step via one of the following methods:
  the amine-compound is provided in its entirety or in part to the adduction step where it is converted into its $CO_2$ adduct, which is then provided to the reaction step, with the hydroxy-functional compound being provided to the reaction step,
  the hydroxy-functional compound is provided in its entirety or in part to the adduction step where it is converted into its $CO_2$ adduct, which is then provided to the reaction step, with the amine-functional compound being provided to the reaction step,
  the hydroxy-functional compound and the amine-functional compound are both provided to the adduction where they are converted in their entirety or in part to their $CO_2$ adducts, which are provided to the reaction step.

In another embodiment the adduction step comprises an absorption step and the elimination step comprises a desorption step, and wherein a stream comprising $CO_2$ is withdrawn from the desorption step and provided to the absorption step and a stream comprising water is withdrawn from the absorption step and provided to the desorption step.

A stream comprising water may be withdrawn from the reaction step and provided to the elimination step in the integrated process.

A separation step may be provided after the reaction step and before the elimination step and independently a further separation step may be provided after the elimination step.

In yet another preferred embodiment of the integrated process, the process comprises the steps of
  providing a starting compound comprising a —NH-A-NH— moiety or a —NH-A-OH moiety, or HO-A-OH to an absorption step where it is combined with $CO_2$ and reacted to form a $CO_2$ adduct,
  providing the $CO_2$ adduct to a reaction step where it is reacted with a further reactant, the reactants in the reaction step being a hydroxy-functional compound selected from the group of alkanolamines and dihydroxyalkylenes, and an amine-functional compound, wherein at least part of the total of hydroxy-functional compounds and amine-functional compounds is provided in the form of a $CO_2$ adduct, to form a product comprising a $CO_2$ adduct of a polypropylene amine compound,
  providing the product comprising a $CO_2$ adduct of a polypropylene amine compound to a desorption step, where it is contacted with a stripping gas, and withdrawing a $CO_2$-containing stripping gas from the desorption step and providing it to the absorption step,
  withdrawing a stripping gas from which $CO_2$ has been absorbed from the absorption step and providing it to the desorption step,
  providing the product from the desorption step to a separation step, which yields a starting material fraction which is provided to the absorption step or to the reaction step, the separation step further yielding a product fraction of polypropylene amine compounds which is withdrawn for the separation step, and a fraction comprising $CO_2$ adducts of polypropylene amine compounds, which is provided to the desorption step or to the reaction step.

Alternatively in yet another preferred embodiment the integrated process may comprise the steps of providing a starting compound comprising a —NH-A-NH— moiety or a —NH-A-OH moiety, or HO-A-OH to an absorption step where it is combined with $CO_2$ and reacted to form a $CO_2$ adduct, providing the $CO_2$ adduct to a reaction step where it is reacted with a further reactant, the reactants in the reaction step being a hydroxy-functional compound selected from the group of alkanolamines and dihydroxyalkylenes, and an amine-functional compound, wherein at least part of the total of hydroxy-functional compounds and amine-functional compounds is provided in the form of a $CO_2$ adduct, to form a product comprising a $CO_2$ adduct of a polypropylene amine compound, providing the product comprising a $CO_2$ adduct of a polypropylene amine compound to a separation step, which yields a starting material fraction which is provided to the absorption step or to the reaction step, with the remainder being provided to a desorption step, in the desorption step contacting the remainder from the separation step with a stripping gas, and withdrawing a $CO_2$-containing stripping gas from the desorption step and providing it to the absorption step, withdrawing a stripping gas from which $CO_2$ has been absorbed from the absorption step and providing it to the desorption step, providing the product from the desorption step to a further separation step which yields a product fraction of polypropylene amine compounds which is withdrawn for the separation step, and a fraction comprising $CO_2$ adducts of polypropylene amine compounds, which is provided to the desorption step or to the reaction step.

Inorganic bases are Lewis or Brønsted bases that do not contain a C—C bond and preferably are strong bases that have a pKb of less than 1.

The reactor(s) employed in the process of the invention can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C. In embodiments where the alkanolamine-functional compound is monoethanolamine or monopropanolamine, 2-amino-1-propanol and/or 1-amino-2-propanol and/or 3-amino-1-propanol the most preferred temperature range is between 230 and 290° C.

The reaction time during the process is in an embodiment between 5 minutes and 15 hours, preferably between 0.5 and 10 hours, more preferably between 1 and 6 hours.

The process can be carried out in one or multiple batch reactors, possibly fed-batch operation, or in a continuously operating system in one reactor or in a cascade of continuous flow reactors, optionally with multiple feeding points. Though several steps are identified in this document, such as e.g. the absorption step, the reaction step, and the desorption step and indicated as different steps they can be carried out in a single vessel or sometimes steps can be even combined like a reaction and elimination step can be in a reactive separation process in which at least partly they are done simultaneously. The reaction and separation also can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

EXAMPLES

Materials and Methods:

General: The reactions were carried out in 7 mL pressure vessels without stirring. The reactants were charged to the pressure vessels, the vessels were sealed and, for reactions using $CO_2$, $CO_2$ was added with a syringe pump. The reaction vessels were placed in an oven and heated to the specified reaction temperature (200-280° C.) for the stated reaction time (1 to 6 h). At the end of the reactions, the vessels were cooled to 50° C. and carefully depressurized. The end-cap was opened and a sample of the reaction mixture was solved in $H_2O$ for analysis by Gas Chromatography—Flame Ionization Detector (GC-FID). The results are reported as GC peak area-%. Identity of GC peaks was determined by GC-MS (CI) Gas Chromatography-Mass Spectrometry (Chemical Ionization).

Example 1

Reaction of Propanolamine in the Presence of CO2

The reaction of this Example 1, reacting 2 equivalents of propanolamine (PA) in the presence of CO2, can be represented by below reaction formula:

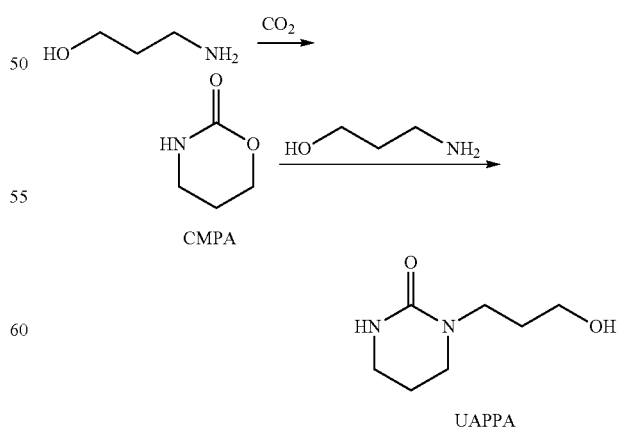

L-propanolamine was reacted with $CO_2$ (molar ratio 1:1) for 1 h at 200° C., and for 2 h at 250° C.

The reactions were incomplete at these reaction times/temperatures as starting material was still present. Propanolamine reacts with $CO_2$ to form the six-membered cyclic carbamate CMPA, which is the main product at 200° C. CMPA reacts with additional propanolamine to form UAPPA, which is the main product at 250° C.

The results are presented in below Table 1 wherein the amounts for the starting material (PA propanolamine), the intermediate (CMPA) and the product (UAPPA) correspond with GC area %.

TABLE 1

Reaction of propanolamine with $CO_2$

|  | Example | |
| --- | --- | --- |
|  | 1A | 1B |
| Reaction time | 1 h | 2 h |
| Temperature | 200° C. | 250° C. |
| PA | 74.4 | 24.4 |
| CMPA | 22.0 | 4.0 |
| UAPPA | 2.5 | 35.6 |

It can be concluded that with the right conditions it is possible to react two equivalents of propanolamine in the presence of CO2 to provide a (cyclic urea of) aminopropylpropanolamine.

Example 2

Reaction of Propanolamine with Diethylenetriamine in the Presence of CO2

The reaction of this Example 2, reacting propanolamine (PA) with diethylentriamine (DETA) in the presence of CO2, can be represented by below reaction formula:

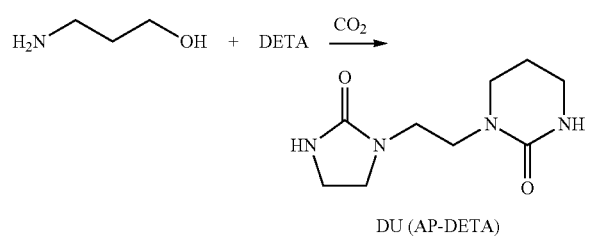

DU (AP-DETA)

For the reaction of DETA with propanolamine 0.52 g DETA, 0.37 g PA and 0.44 g $CO_2$ were charged to the reaction vessels (molar ratio 1:1:2). The reaction was carried out for 2 h at 250° C.

For the reaction of UDETA with propanolamine 1.3 g UDETA, 0.75 g PA and 0.44 g $CO_2$ were charged to the reaction vessels (molar ratio 1:1:1) and the reactions were run for 2 h at 280° C.

The results are presented in below Table 2 wherein the amounts for the starting material (PA, CMPA, and (U)DETA), and the product (DU-(AP-DETA)) correspond with GC area %.

TABLE 2

Reaction of DETA/UDETA with PA.

|  | Example | |
| --- | --- | --- |
|  | 2A | 2B |
| Amine | DETA | UDETA |
| temperature (° C.) | 250 | 280 |
| reaction time (h) | 2 | 2 |
| molar ratio (amine/PA/$CO_2$) | 1:1:2 | 1:1:1 |
| PA | 10.6 | 3.3 |
| CMPA | 4.2 | 1.0 |
| (U)DETA | 40.4 | 37.2 |
| DU (AP-DETA) | 13.0 | 27.1 |

It can be concluded that it is possible to react propanolamine with diethylenetriamine in the presence of CO2 to provide a (cyclic diurea of) aminopropylldiethylenetriamine Example 3

Reaction of Propanolamine with Ethylenediamine

The reaction of this Example 3, reacting propanolamine (PA) with ethylenediamine (EDA) in the presence of CO2, can be represented by below reaction formula:

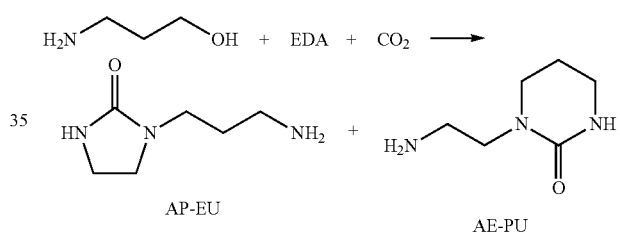

AP-EU          AE-PU

For the first reaction PA was reacted with an excess EDA and $CO_2$ as CO source. 0.6 g EDA, 0.75 g PA and 0.44 g $CO_2$ were charged to the reaction vessels (molar ratio 1/1/1) and the reaction was carried out 280° C. for 4 h.

The final reaction mixture was treated to obtain the product amine in a purified quality and unconverted raw material was isolated. 0.50 g of desired product (AP-EU and AE-PU) was obtained per 1 g EDA added to the batch.

0.1 g of the isolated unconverted EDA was transferred to a next batch, to which another 0.5 g EDA was added with 0.75 g PA and 0.44 g $CO_2$ (to obtain a molar ratio EDA:PA:$CO_2$ of 1/1/1) and again the reaction was carried out 280° C. for 4 h.

The final reaction mixture was treated again to obtain the product amine in a purified quality and unconverted raw material was isolated. Now 0.54 g of desired product (AP-EU and AE-PU) was obtained per 1 g total amount of EDA added.

This Example shows the reaction between propanolamine and EDA in the presence of $CO_2$ as a carbon oxide delivering agent to give (two ureas of) aminopropylethyleneamine (aminopropylethyleneurea and aminoethylpropyleneurea). The Example also shows the benefit of recycling materials in the process.

Example 4

Reaction of Propanolamine with Piperazine in the Presence of CO2

The reactions of Examples 4A and 4B, reacting propanolamine (PA) with piperazine (PIP) in the presence of $CO_2$, can be represented by below reaction formula:

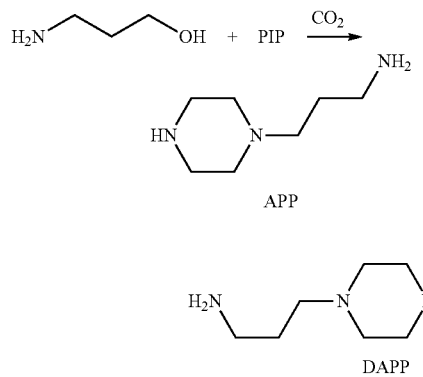

For reaction 4A; 0.43 g PIP, 0.375 g PA, and 0.44 g $CO_2$ (molar ratio PIP/PA/$CO_2$ 1/1/2) were charged to a pressure vessel and reacted for 4 h at 220° C.

For reaction 4B; 0.86 g PIP, 0.75 g PA, 0.22 g $CO_2$ and 0.18 g $H_2O$ (molar ratio PIP/PA/$CO_2$/$H_2O$ 1/1/0.5/1) were charged to a pressure vessel and reacted for 4 h at 220° C.

The results are presented in below Table 4. In Table 4 the amounts for the starting material (PA, CMPA, PIP), and the products (APP, DAPP) correspond with GC area %.

TABLE 4

Reaction of PIP with PA and $CO_2$.

| | Example | |
| --- | --- | --- |
| | 4A | 4B |
| temperature (° C.) | 220 | 220 |
| reaction time (h) | 4 | 4 |
| molar ratio (PIP/PA/$CO_2$) | 1/1/2 | 1/1/0.5 |
| $H_2O$ | — | 1 equiv |
| PA | 6.62 | 8.0 |
| PIP | 18.58 | 17.2 |
| APP | 16.33 | 17.3 |
| CMPA | 7.91 | 3.8 |
| DAPP | 1.79 | 2.0 |

Examples 4A and 4B demonstrate that a reaction can also be performed between propanolamine and piperazine. Comparison of the examples also demonstrates that addition of $H_2O$ to the reaction mixture allows a significant reduction in $CO_2$ amounts and still results in slightly higher yields of the products APP and DAPP.

Example 5

Reaction of Piperazine with Isopropanolamine in the Presence of CO2

The reaction of Example 5, reacting isopropanolamine (PA) with piperazine (PIP) in the presence of CO2, can be represented by below reaction formula:

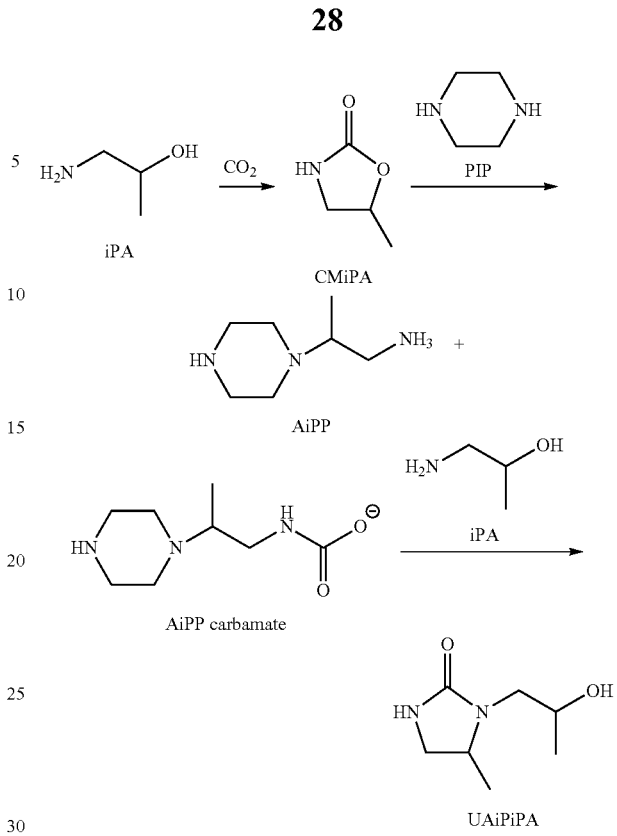

0.43 g piperazine (PIP) was reacted with 0.38 g isopropanolamine (iPA) and 0.44 g $CO_2$ (molar ratio 1:1:2) for 4 h at 220° C. First, a 5-membered cyclic carbamate of iPA is formed (CiMPA) as intermediate from iPA and $CO_2$ and this reacts further with piperazine to yield aminoisopropylpiperazine (AiPP) as main product along with some aminoisopropylpiperaine carbamate (AiPP carbamate). The cyclic urea of aminoisopropylisopropanolamine (UAiPiPA) is formed in a side reaction from reaction of CMiPA with iPA.

Example 6

The Reaction of Diethylenetriamine Urea (UDETA) with Isopropanolamine (iPA) in the Presence of CO2

The reaction of Example 6, reacting diethylenetriamine urea (UDETA) with isopropanolamine (iPA) in the presence of $CO_2$ can be represented by below reaction formula

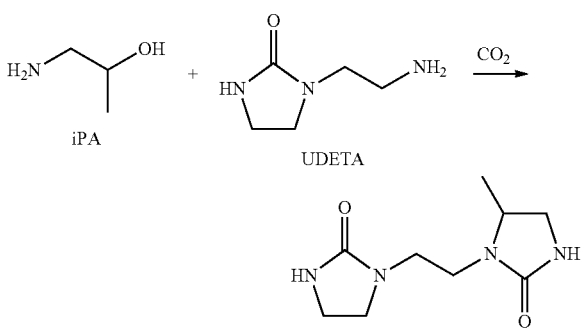

1.30 g diethylenetriamine urea (UDETA) was reacted with 0.75 g iPA and 0.44 g $CO_2$ (molar ratio 1:1:1) for 4 h at 280° C. to yield the cyclic diurea of aminoisopropyldiethylenetriamine (DU (AiPDETA)) along with the side product UAiPiPA.

Example 7

The reaction of Ethylenediamine (EDA) with Ethyleneurea (EU) and Isopropanolamine The reaction of Example 7, reacting ethylenediamine (EDA) with ethyleneurea (EU) and isopropanolamine can be represented by below reaction formula.

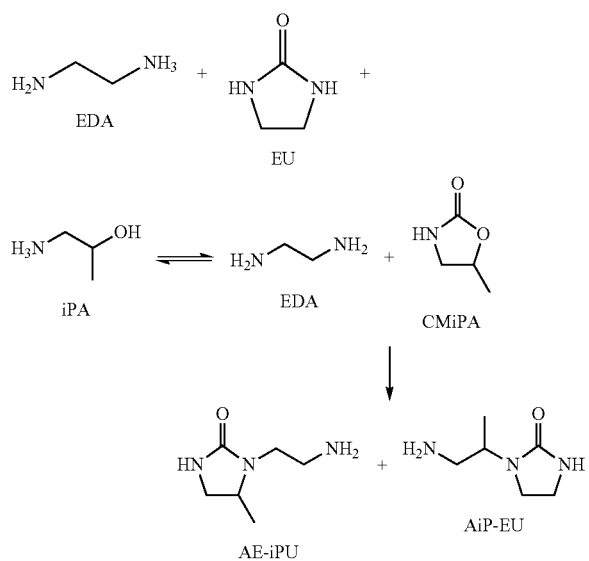

0.45 g ethylenediamine (EDA) and 1.51 g ethyleneurea (EU) were reacted with 0.75 g iPA (molar ratio 0.75:1.75:1) for 4 h at 280° C. In this reaction EU functioned as sole CO source. Only little CiMPA and some UAiPiPA were formed, while the main products were aminoethyl isopropyleneurea (AE-iPU) and aminoisopropyl ethyleneurea (AiP-EU), whose peaks were not separated by GC and are reported as sum.

The results of Examples 5 to 7 are presented in Table 5.

TABLE 5

| Reactions of iPA | | | |
|---|---|---|---|
| | Example | | |
| | 5 | 6 | 7 |
| temperature (° C.) | 220 | 280 | 280 |
| reaction time (h) | 4 | 4 | 4 |
| starting material | PIP/iPA/CO₂ | UDETA/iPA/CO₂ | EDA/EU/iPA |
| molar ratio | 1/1/2 | 1/1/1 | 0.75/1.75/1 |
| iPA | 15.2 | 4.9 | 11.9 |
| CMiPA | 12.0 | 0.9 | 0.6 |
| UAiPiPA | 3.6 | 27.0 | 6.2 |
| PIP | 42.0 | | |
| AiPP | 13.9 | | |
| AiPP carbamate | 2.6 | | |
| UDETA | | 21.0 | |
| DU (AiPDETA) | | 33.4 | |

TABLE 5-continued

| Reactions of iPA | | | |
|---|---|---|---|
| | Example | | |
| | 5 | 6 | 7 |
| EDA | | | 19.6 |
| EU | | | 27.1 |
| AE-iPU + AiP-EU | | | 22.8 |

The Examples 5 to 7 demonstrate that isopropanolamine forms a cyclic 5-membered carbamate with $CO_2$ and that this cyclic carbamate reacts with amines to elongate these with a branched isopropylamine unit. The reactions were found to occur on the methyl-substituted carbon of the cyclic urea.

The presence of a methyl substituent in the starting material, intermediates and products give rise to a chiral center. Because a racemic mixture of D- and L-2-propanolamine was used as starting material also racemic mixtures of the products were formed. These were sometimes separated during GC analysis, however, enantiomers were not individually assigned and therefore during quantification the peaks of enantiomers were summed up.

Example 8

Reaction of Octylamine with Propanolamine or Isopropanolamine

The reactions of Example 8A and 8B reacting octylamine with propanolamine or isopropanolamine in the presence of $CO_2$ can be represented by the below reaction formula:

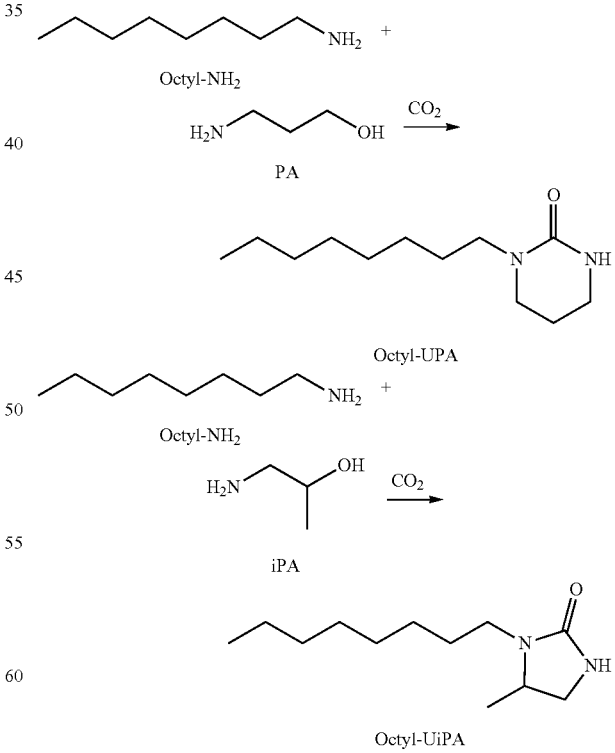

0.64 g octylamine was reacted with either 0.38 g propanolamine (8A) or 0.38 g isopropanolamine (8B) and 0.44 g $CO_2$ (molar ratio 1:1:2) for 4 h at 280° C. to yield octylproplyeneurea (octyl-UPA) and octyl-isopropyleneurea (octyl-UiPA), respectively, as main products.

The results are presented in below Table 6.

TABLE 6

Reactions of octylamine

| | Example | |
|---|---|---|
| | 8A | 8B |
| temperature (° C.) | 280 | 280 |
| reaction time (h) | 4 | 4 |
| starting material | Octyl-NH$_2$/PA/CO$_2$ | Octyl-NH$_2$/iPA/CO$_2$ |
| molar ratio | 1/1/2 | 1/1/2 |
| Octyl-NH$_2$ | 57.7 | 61.2 |
| PA | 10.6 | |
| CMPA | 0.3 | |
| UAPPA | 4.8 | |
| Octyl-UPA | 11.2 | |
| iPA | | 13.6 |
| CMiPA | | 0.8 |
| UAiPiPA | | 2.1 |
| Octyl-UiPA | | 7.7 |

Examples 8A and 8B demonstrate that the chain elongation of amines with a propanolamine or isopropanolamine units in the presence of carbon dioxide also works for fatty amines. This means that an aminopropyl unit can be added to fatty amines using the process of the invention.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process of preparing propylene amines of the formula NH$_2$-(A-NH—)$_p$R, said method comprising:
   reacting
   (i) at least one of a hydroxy-functional compound chosen from alkanolamine-functional compounds and dihydroxyalkylene compounds, and
   (ii) an amine-functional compound, in the presence of
   (iii) a carbon oxide delivering agent,
   wherein at least one of the (i) a hydroxy-functional compound, the (ii) amine-functional compound, and/or the (iii) carbon oxide delivering agent comprises at least one alkylene unit (A) that is a linear or branched propylene unit,
   wherein in the formula NH$_2$-(A-NH—)$_p$R
   each A is an independently selected alkylene unit with the proviso that at least one alkylene unit A is the linear or branched propylene unit,
   R is a hydrogen atom or an alkyl group,
   p is at least 1 when R is an alkyl group and p is at least 2 when R is a hydrogen atom, and one or more units —NH-A-NH— may be present as a cyclic urea unit

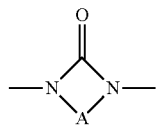

if p is at least 1 or a cyclic unit

if p is at least 2, or
   a carbonyl bond is present between two units NH-A-NH— if p is at least 2, and
   wherein the molar ratio of the (iii) carbon oxide delivering agent to the (ii) amine-functional compound is between 0.7:1 and 20:1.

2. The process of claim 1, wherein a molar ratio of the (i) hydroxy-functional compound to the (ii) amine-functional compound is at least about 0.7:1.

3. The process of claim 1, wherein a molar ratio of the (i) hydroxy-functional compound to the (ii) amine-functional compound is from about 0.05:1 to about 0.7:1 and a molar ratio of the (iii) carbon oxide delivering agent to the (ii) amine-functional compound is at least 10% higher than the molar ratio of the (i) hydroxy-functional compound to the (ii) amine-functional compound.

4. The process of claim 1 wherein the (i) hydroxy-functional compound is an alkanolamine-functional compound and wherein the alkanolamine-functional compound and the (iii) carbon oxide delivering agent are at least partly added to the reaction as a carbamate adduct.

5. The process of claim 1 wherein the (ii) amine-functional compound and the (iii) carbon oxide delivering agent are at least partly added to the reaction as a urea adduct.

6. The process of claim 1 wherein the (ii) amine functional compound is a primary amine or a cyclic secondary amine compound.

7. The process of claim 1 wherein the (ii) amine-functional compound is of the formula R—NH$_2$ and R is an alkyl group comprising 6 to 22 carbon atoms.

8. The process of claim 1 wherein the reaction of (i)-(iii) prepares a cyclic alkylene urea, and wherein the process further comprises the step of converting the obtained cyclic alkylene urea into its corresponding propylene amine.

9. The process of claim 1 wherein the (i) hydroxy-functional compound is an alkanolamine-functional compound of the formula OH-(A-NH—)$_q$H wherein q is at least 1 and the (ii) amine-functional compound is of the formula NH$_2$-(A-NH—)$_r$H wherein r is at least 1, and wherein one or more q or r units is present as a cyclic alkylene urea, cyclic alkylene carbamate or cyclic unit

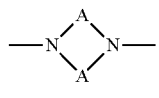

10. The process of claim 1 wherein the (i) hydroxy-functional compound is an alkanolamine-functional compound of the formula OH-(A-NH—)$_q$H wherein q is at least 1, wherein the (ii) amine-functional compound is of the formula NH$_2$-(A-NH—)$_r$H wherein r is at least 1 and is free of cyclic unit, and wherein reacting (i)-(iii) is carried out in the presence of (iv) water, with a molar ratio of (iv) water to the (iii) carbon oxide delivering agent of from about 0.01:1 to about 2:1.

11. The process of claim 10 wherein the molar ratio of the (iv) water to the (iii) carbon oxide delivering agent is from about 0.05:1 to about 1:1.

12. The process of claim 1 wherein the (ii) amine-functional compound comprises a terminal cyclic unit

and wherein reacting (i)-(iii) is carried out in a liquid that comprises (iv) water.

13. The process of claim 12 wherein the liquid comprises at least about 75 wt-% of water based on total liquid weight.

14. The process of claim 12 wherein a molar ratio of the (iv) water to the (ii) amine-functional compound is greater than about 0.2:1.

15. The process of claim 1 wherein (iv) water is added or removed during the process intermittently, semi-continuously or continuously.

16. The process of claim 1 further comprising the step of manufacturing the (iii) carbon oxide delivering agent, wherein the (iii) carbon oxide delivering agent is a cyclic urea adduct of an alkyleneamine or alkanolamine compound that comprises at least one NH-A-NH— moiety and at least two alkylene moieties, wherein at least one of the units A and alkylene units is a propylene unit, wherein the step of manufacturing comprises reacting the alkyleneamine or alkanolamine compound with CO$_2$ in the presence of an auxiliary compound selected from ethylenediamine (EDA), propylenediamine (PDA), monoethanolamine (MEA), monopropanolamine (MPA) and mixtures thereof, and wherein the molar ratio of the auxiliary compound to the (ii) amine-functional compound is at least about 0.02:1.

17. The process of claim 1 further comprising the step of manufacturing the (iii) carbon oxide delivering agent, wherein the (iii) carbon oxide delivering agent is a cyclic urea adduct of an alkyleneamine compound having a linear —NH-A-NH— group, wherein the step of manufacturing comprises the steps of
   in an absorption step contacting a liquid medium comprising the alkyleneamine compound with a CO$_2$-containing gas stream at a first pressure of from about 1 to about 20 bar and at a first temperature, resulting in the formation of a liquid medium into which CO$_2$ has been absorbed,
   bringing the liquid medium into which CO$_2$ has been absorbed to cyclic urea formation conditions comprising a second pressure and a second temperature of at least about 120° C., and
   in an urea formation step, forming a cyclic urea adduct of the alkyleneamine compound under the urea formation conditions, thereby giving the (iii) carbon oxide delivering agent, wherein a total pressure at the end of the urea formation step is at most about 20 bar, and wherein the first temperature in the absorption step is lower than the second temperature in the urea formation step.

18. The process of claim 1 wherein the propylene amines are further defined as a mixture of straight-chain higher propyleneamines and non-straight-chain higher propyleneamines selected from branched higher propyleneamines and cyclic higher propyleneamines, or urea derivatives thereof, of the formula NH$_2$-(A-NH—)$_p$R, wherein the (i) hydroxy-functional compound is an alkanolamine-functional compound, and wherein
   the (ii) amine-functional compound comprises
      a combination of a straight-chain amine-functional compound and a non-straight-chain amine-functional compound and the alkanolamine-functional compound is a straight-chain alkanolamine-functional compound, or
   the (ii) amine-functional compound is a straight-chain amine-functional compound and the alkanolamine-functional compound comprises a combination of a straight-chain alkanolamine-functional compound and a non-straight-chain alkanolamine-functional compound, or
   the amine-functional compound comprises a combination of a straight-chain amine-functional compound and a non-straight-chain amine-functional compound and the alkanolamine-functional compound comprises a combination of a straight-chain alkanolamine-functional compound and a non-straight-chain alkanolamine-functional compound.

19. The process of claim 1 wherein the process is integrated and comprises the steps of;
   an adduction step providing a CO$_2$ adduct of a starting compound comprising a —NH-A-NH— moiety or a —NH-A-OH moiety, or HO-A-OH,
   in a reaction step reacting the (i) hydroxy-functional compound which is selected from the group of alkanolamines, dihydroxyethane and dihydroxypropane with the (ii) amine-functional compound, wherein at least part of the total of hydroxy-functional compounds and amine-functional compounds is provided in the form of a CO$_2$ adduct, to form CO$_2$ adduct of a product propyleneamine compound,
   in an elimination step converting the CO$_2$ adduct of the product polypropylene amine compound to a corresponding product propylene amine compound,
   wherein a fraction comprising a recycle compound is provided from the end of the reaction step or the elimination step to the adduction step or to the reaction step,
   wherein the recycle compound comprises a —NH-A-NH— moiety or a —NH-A-OH moiety, or HO-A-OH, or a CO$_2$ adduct thereof, and has per molecule on average fewer of the total of —NH-A-NH— moieties and —NH-A-OH moieties than the product propyleneamine compound.

20. The process of claim 1 wherein the (iii) carbon oxide delivering agent is chosen from carbon dioxide, urea, linear and cyclic alkylene ureas, mono or di-substituted alkylene ureas, alkyl and dialkyl ureas, linear and cyclic carbamates and organic carbonates, and derivatives or precursors thereof selected from carbonate salts, bicarbonate salts and carbamic acids and their associated salts.

* * * * *